(12) United States Patent
Tamaoki et al.

(10) Patent No.: US 7,838,286 B2
(45) Date of Patent: Nov. 23, 2010

(54) INCUBATOR

(75) Inventors: Yuichi Tamaoki, Gunma-ken (JP); Yasushi Sakata, Tatebayashi (JP); Hidetoshi Shinya, Gunma-ken (JP); Hiroki Busujima, Ota (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 805 days.

(21) Appl. No.: 10/947,553

(22) Filed: Sep. 23, 2004

(65) Prior Publication Data

US 2005/0084956 A1    Apr. 21, 2005

(30) Foreign Application Priority Data

Sep. 26, 2003   (JP)   ............... 2003-334702

(51) Int. Cl.
  C12M 1/00    (2006.01)
  C12M 3/00    (2006.01)
(52) U.S. Cl. .................................. 435/303.1
(58) Field of Classification Search ... 435/289.1–303.1; 422/99
   See application file for complete search history.

(56) References Cited

U.S. PATENT DOCUMENTS

| | | | | |
|---|---|---|---|---|
| 5,169,217 A | * | 12/1992 | Orchard et al. ........... 312/223.1 |
| 5,352,414 A | * | 10/1994 | Rothenberg ................ 422/101 |
| 5,519,188 A | * | 5/1996 | Yuichi et al. ................ 219/407 |
| 5,783,439 A | * | 7/1998 | Reichler et al. .......... 435/286.1 |
| 5,882,918 A | * | 3/1999 | Goffe ....................... 435/286.6 |
| 6,255,103 B1 | * | 7/2001 | Tamaoki et al. .......... 435/303.1 |
| 2004/0215362 A1 | * | 10/2004 | Kokubo et al. ............. 700/130 |

OTHER PUBLICATIONS

The website NuAire, Inc.http://web.archive.org/web/20030218141437/www.nuaire.com/incubator/ir.html. Internet Archive Dec. 11, 2002. pp. 1-2.*

* cited by examiner

*Primary Examiner*—Walter D Griffin
*Assistant Examiner*—Shanta G Doe
(74) *Attorney, Agent, or Firm*—Kratz, Quintos & Hanson, LLP

(57) ABSTRACT

An entry of air from the outside of an incubator into an incubation room is prevented. The incubator comprises an adiabatic box main body having an opening on a front face thereof, an adiabatic door mounted to the adiabatic box main body to be opened/closed, a transparent inner door which closes the opening to be opened, and a storeroom surrounded with the inner door and the adiabatic box main body to incubate samples such as cells or microbes. The adiabatic box main body comprises a metal outer box, a metal inner box, a heat insulating material arranged in the outer box between the outer box and the inner box, and an air layer arranged more inside than the heat insulating material. Pressure of the storeroom is set higher than that of an outside space of the incubator.

2 Claims, 5 Drawing Sheets

INCUBATOR

BACKGROUND OF THE INVENTION

The present invention relates to a carbon dioxide gas ($CO_2$) incubator or a multigas incubator as an incubator to incubate cultures (samples) such as cells or microbes.

The incubator maintains a temperature and a $CO_2$ concentration constant therein (in incubation room) and makes the inside sterile to incubate cultures (samples) such as cells or microbes which are incubation targets. Thus, the inside of the incubator must be subjected to periodic sterilization treatment. To incubate the samples, a heater and its controller are disposed to adjust a temperature in the incubation room (storeroom).

Additionally, as disclosed in Japanese Patent Application Laid-Open Nos. 8-322552 and 2000-166536, there have been incubators each of which comprises an air layer (air jacket) around an incubation room to promote heat insulation thereof from the outside of the incubator and heat transfer by natural convection.

On the other hand, the important and precious cells or microbes which are incubation targets are placed and incubated in the incubator. However, since there are a plurality of joints or an infinite number of very small holes in a metal inner box which defines the air jacket and the incubation room, the air jacket and the incubation room are not cut off from each other in terms of an air flow. Consequently, it is impossible to block an entry of contaminated air into the incubation room from the outside due to an opening/closing operation of an inner door, air flow noncutting-off or the like. Hence, there is a fear that even when sterilization treatment is executed for each incubation, the entered contaminated air may cause breeding of saprophytic bacterias in the samples (cultures) to be incubated or impossibility of incubating normal samples. Furthermore, since the incubator may inject a $CO_2$ gas into the incubation room, certain gas leakage inevitably occurs because of a pressure fluctuation which accompanies the injection.

SUMMARY OF THE INVENTION

It is an object of the present invention to provide an incubator which can prevent an entry of air into an incubation (storage) room from the outside of the incubator. It is another object of the invention to block an entry of outside air from a rear side of an incubator to its front.

According to the present invention, an incubator (1) comprises an adiabatic box main body (2) having an opening (2A) on a front face thereof, an adiabatic door (3) mounted to the adiabatic box main body (2) to be opened/closed, a transparent inner door (7) which closes the opening (2A) to be opened, and a storeroom (4) surrounded with the inner door (7) and the adiabatic box main body (2) to incubate samples such as cells or microbes. The adiabatic box main body (2) comprises a metal outer box (11), a metal inner box (12), a heat insulating material (14) arranged in the outer box between the outer box (11) and the inner box (12), and an air layer (15) arranged more inside than the heat insulating material (14). Pressure of the storeroom (4) is set higher than that of an outside space of the incubator (1).

The incubator (1) of the invention further comprises an exhaust tube (21) with an exhaust fan (22) one end opening (21A) of which is positioned in the air layer (15) and the other end opening (21B) of which is positioned in the outside space (24) of the incubator (1).

In the incubator (1) of the invention, an exhaust filter (23) for bacteria elimination is disposed in the exhaust tube (21).

The incubator (1) of the invention further comprises a suction tube (31) with a suction pump (32) one end opening (31B) of which is positioned in the storeroom (4) and the other end opening (31A) of which is positioned in the outside space (34) of the incubator.

In the incubator (1) of the invention, a suction filter (33) for bacteria elimination is disposed on the storeroom side more than the suction pump (32) of the suction tube (31).

The incubator (1) of the invention further comprises heaters (13A), (13B) arranged in a bottom surface of the inner box (12) and outside both left and right side faces to heat the storeroom (4), and a humidifying tray (6) arranged in the bottom surface of the inner box (12) to store humidification water.

In the incubator (1) of the invention, in heating means (13), the heater (13A) arranged in the bottom surface of the inner box and the heaters (13B), (13B) arranged in both left and right side faces are constituted of different circuits.

According to the present invention, an incubator (1) comprises an adiabatic box main body (2) having an opening (2A) on a front face thereof, a transparent inner door (7) which closes the opening (2A) to be opened, and a storeroom (4) surrounded with the inner door (7) and the adiabatic box main body (2) to incubate samples such as cells or microbes. The storeroom (4) comprises an air passage (17) through which air thereof is circulated, and a circulation fan (18) arranged in the air passage (17). A suction tube (31) with a suction pump (32) is disposed one opening end (31B) of which is positioned in the air passage (17) and the other end opening (31B) of which is positioned in an outside space (34) of the incubator.

According to the present invention, an incubator (1) comprises an adiabatic box main body (2) having an opening (2A) on a front face thereof, a transparent inner door (17) mounted to the adiabatic box main body (2) to be opened/closed and to close the opening (2A) to be opened, and a storeroom (4) surrounded with the inner door (7) and the adiabatic box main body (2) to incubate samples such as cells or microbes. The adiabatic box main body (2) comprises a metal outer box (11), a metal inner box (12), a heat insulating material (14) arranged in the outer box between the outer box (11) and the inner box (12), and an air layer (15) arranged more inside than the heat insulating material (14). A partition wall (40) is disposed in the adiabatic box main body (2) to divide outside spaces (41), (42) of the incubator into front and rear portions.

In the incubator (1) of the invention, pressure of the space (42) after the partition wall (40) of the incubator (1) is set lower than that of the storeroom (4).

In the incubator (1) of the invention, a sealing member (2B) is disposed in the opening of the adiabatic box main body (2) to seal the transparent inner door (17) to the main body (2).

DETAILED DESCRIPTION OF THE PREFERRED EMBODIMENTS

Next, the preferred embodiments of the present invention will be described in detail with reference to the accompanying drawings.

Embodiment 1

Figure 1:
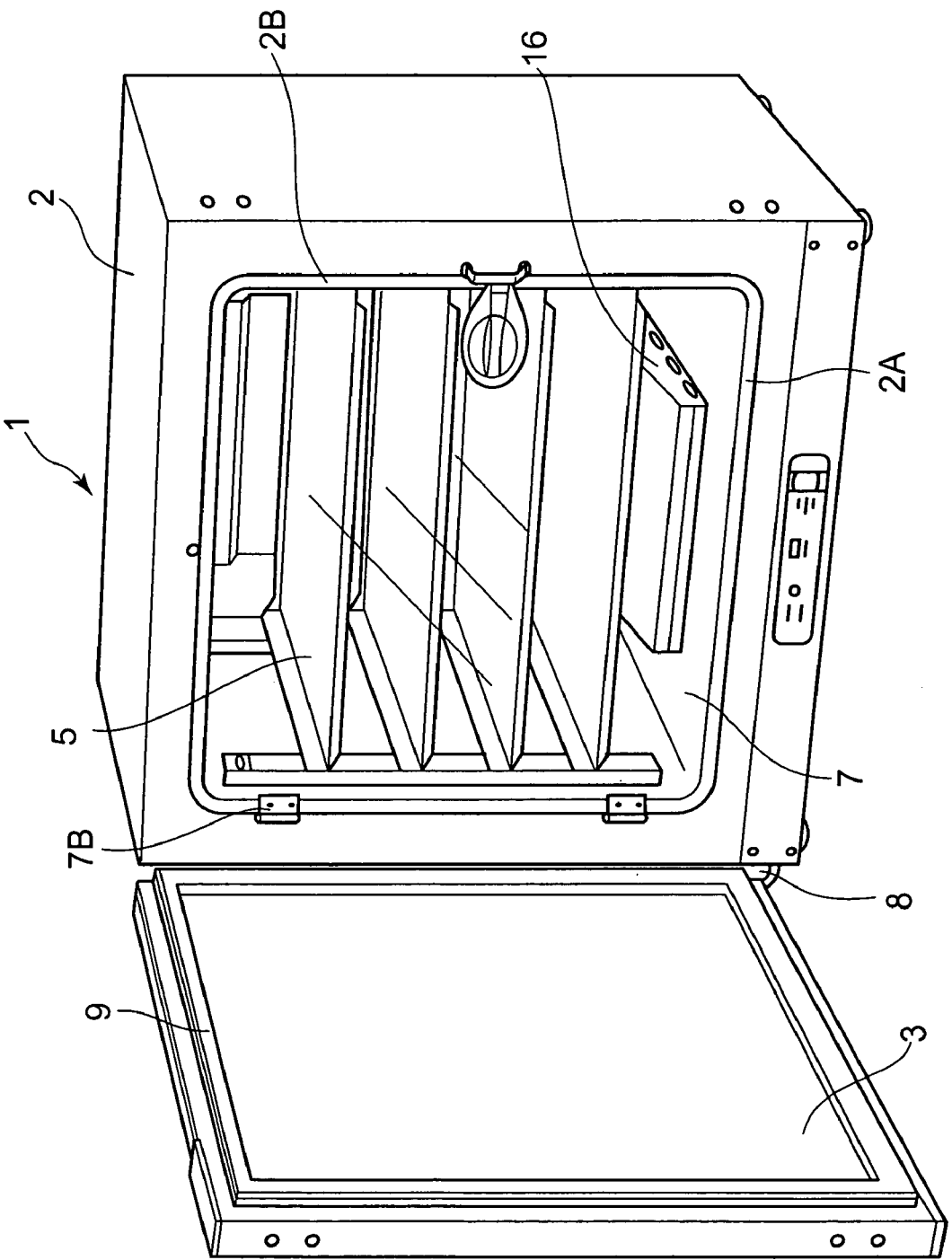
FIG. 1 is a perspective view of an incubator of the present invention in a state in which an adiabatic door is opened.
Figure 2:
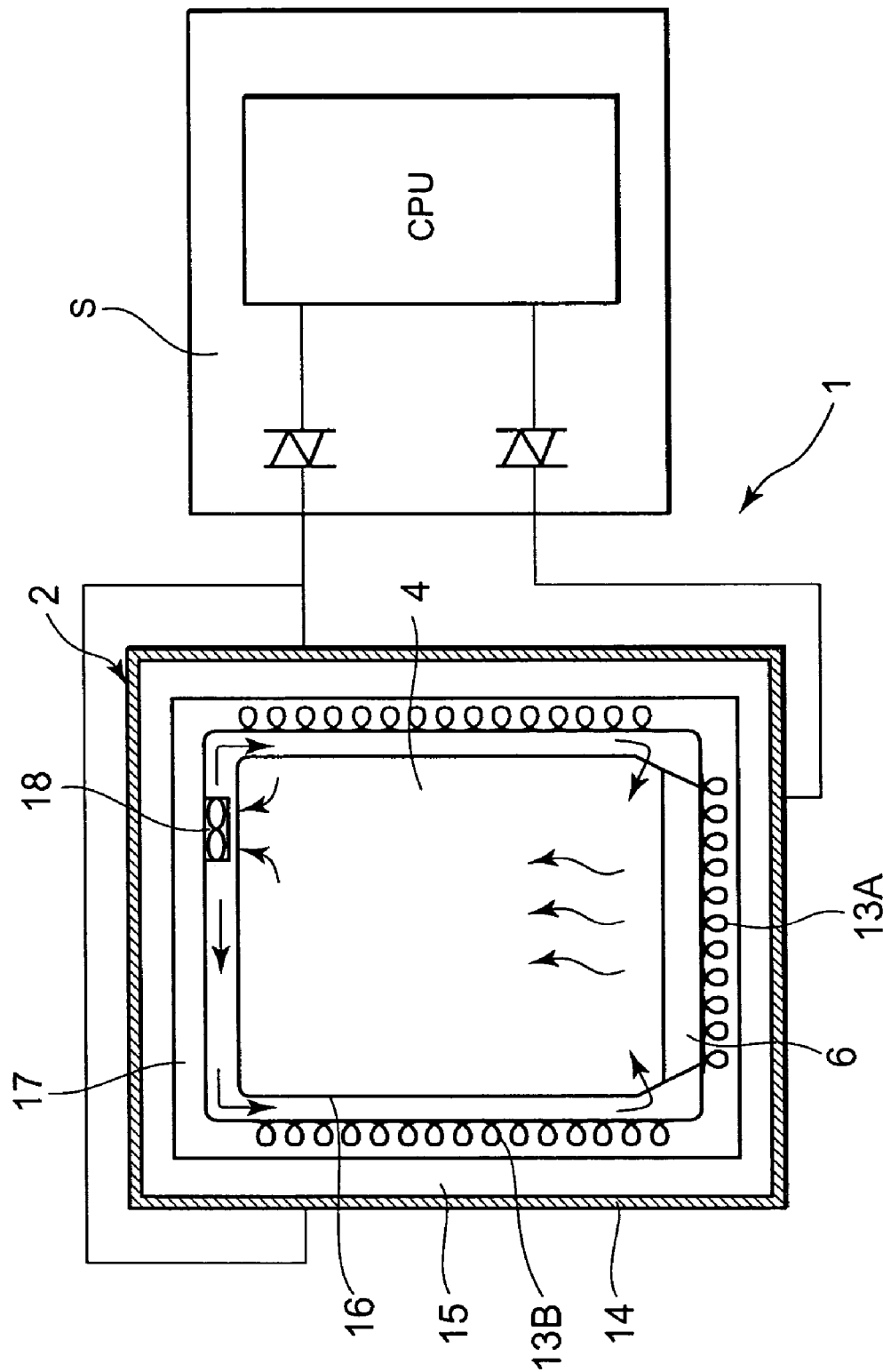
FIG. 2 is a sectional view of the incubator of the invention seen from a front which comprises a controller and a heater.
Figure 3:
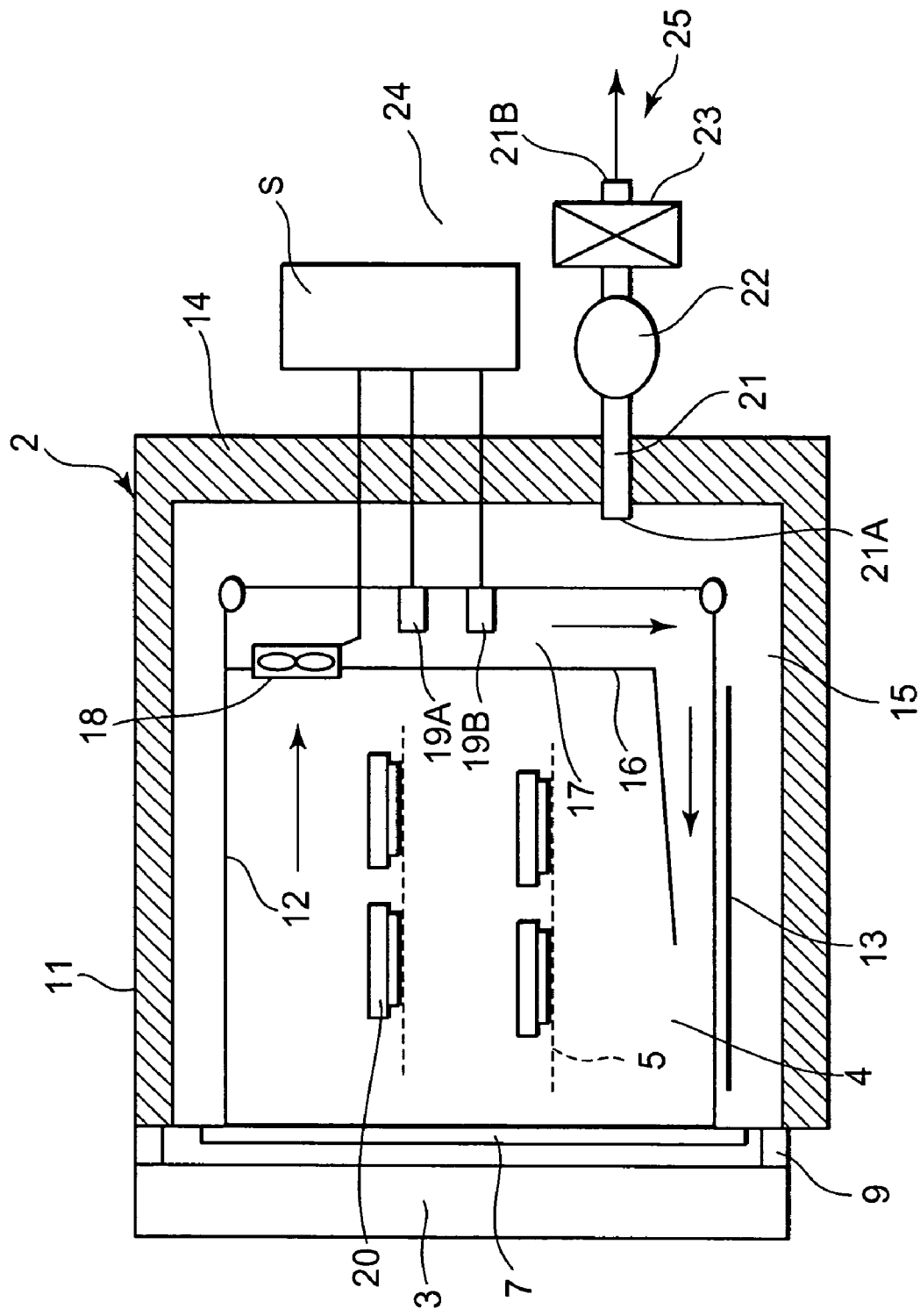
FIG. 3 is a sectional view of an incubator seen from the right according to a first embodiment of the present invention.

An incubator 1 of a first embodiment of the present invention comprises a left-open type door as shown in FIGS. 1, 2 and 3, and an adiabatic box main body 2 having an opening 2A on its front and an adiabatic door 3 which closes the opening 2A to be opened constitute an incubation room 4 therein. The inside of the incubation room 4 is divided into upper and lower portions by a plurality of shelves 5. A humidifying tray 6 which stores water for humidification is arranged in a bottom surface of the incubation room. The humidifying tray 6 is heated by heating means 13B arranged outside the bottom surface of a metal, e.g., stainless steel, inner box 12 to evaporate water.

A reference numeral 7 denotes a transparent inner door which opens/closes the front opening 2A. A reference numeral 7B denotes a pair of upper and lower hinges which fix the inner door 7 to the adiabatic box main body 2 to be opened/closed. A reference numeral 8 denotes a pair of upper and lower hinges (external hinges mounted from the outside) which fix the adiabatic door 3 to the adiabatic box main body 2 to be opened/closed. A reference numeral 9 denotes a gasket with a magnet which is disposed on the backside of the adiabatic door to bond and seal the adiabatic door 3 to the adiabatic box main body 2. In the opening of the adiabatic box main body 2, a sealing member 2B is disposed to seal the transparent inner door 7 to the main body 2.

In FIG. 3, the adiabatic box main body 2 comprises a metal outer box 11, a stainless steel inner box 12, a heat insulating material 14 arranged in the outer box 11 between the outer box 11 and the inner box 12, and an air layer 15 arranged more inside than the heat insulating material 14. Heaters 13B are arranged in both left and right side faces of the inner box 12 of the storeroom 4 to heat the same. A partition plate 16 is arranged with certain spaces from the bottom surface and the backside of the inner box 12. The partition plate 16, and the bottom surface and the backside of the inner box 12 constitute an air passage 17 to circulate air in the storeroom 4. The humidifying tray 6 is arranged in the air passage 17.

In the air passage 17, a circulation fan 18 is arranged, and a temperature sensor 19A and a humidity sensor 19B are arranged to detect a temperature and humidity of the storeroom 4. The circulation fan 18, the temperatures sensor 19A, the humidity sensor 19B, the heaters 13A, 13B, and the like are controlled by a controller S. In the heading means 13, the heater 13A arranged in the bottom surface of the inner box and the heaters 13B, 13B arranged on both left and right side faces of the inner box are constituted of different circuits. A glass container 20 with a cap is mounted on each shelf 5 to receive samples such as cells or microbes therein.

The incubator 1 of FIG. 3 is constituted in such a manner that an exhaust tube 21 with an exhaust fan 22 one end opening 21A of which is positioned in the air layer 15 and the other end opening 21B of which is positioned in an outside space 24 of the incubator 1 is disposed to increase pressure of the storeroom 4 more than that of the outside space, and an exhaust filter 23 for bacteria elimination is disposed on a downstream side of the exhaust fan 22 of the exhaust tube 21. The exhaust tube 21, the exhaust fan 22, and the exhaust filter 23 constitute pressure adjustment means 25.

In FIG. 3, by arranging the exhaust fan 22 and the exhaust filter 23 of the pressure adjustment means 25 outside the incubator 1, it is possible to independently carry out mounting or maintenance work of the pressure adjustment means.

According to the pressure adjustment means 25 of the first embodiment, since the pressure of the storeroom (incubation room) 4 is higher than that of the outside space 24 of the incubator 1, an entry of air from the air layer 15 into the incubation room 4 is blocked even when the air is discharged from the incubation room to the air layer 15 formed around the same. Thus, no air flow is generated from the outside space 24 of the incubator 1 to the incubation room 4, and an entry of contaminated outside air can be prevented. Since the air of the air layer 15 is discharged through the exhaust tube 21, pressure of the air layer 15 can be set lower compared with that of the incubation room 4. An entry of the air of the air layer 15 into the incubation room 4 can be blocked even if there is a small hole in the inner box 12 and the air leaks from the incubation room 4 to the air layer 15. Moreover, since the air of the air layer 15 discharged by the exhaust filter 23 through the exhaust tube 21 to the outside can be subjected to bacteria elimination, even if the air leaks from the incubation room 4 in which bacterias have been bred to the air layer 15, the air can be discharged from the incubation room 4 to the outside in the bacteria eliminated state, and thus the incubator is advantageous for safety and hygiene. The transparent inner door 7 can be surely sealed to the main body 2 by the sealing member 2B disposed in the opening of the adiabatic box main body 2. It is possible to suppress an entry of the outside air to the storeroom (incubation room) 4 which accompanies the opening/closing operation of the adiabatic door 3, and to realize stable incubation in the incubation room.

Heat of the heaters 13A, 13B disposed in the inner box 12 is guided in a wide range in the incubation room 4 through heat transfer of the metal inner box 12, and natural air convection which uses the air of the air layer 15 is generated. Accordingly, heating can be carried out through air transfer even in a direction to a surface of no heater. Besides, humidity in the incubation room can be adjusted by using heat of the heater 13A to heat the humidifying tray 6. By constituting the heater 13A arranged in the bottom surface of the inner box and the heaters 13B arranged in both left and right side faces of the inner box of different circuits, it is possible to heat the humidifying tray 6 independently of heating in the incubation room 4, thereby facilitating adjustment of the temperature and the humidity of the incubator 1.

Embodiment 2

Figure 4:
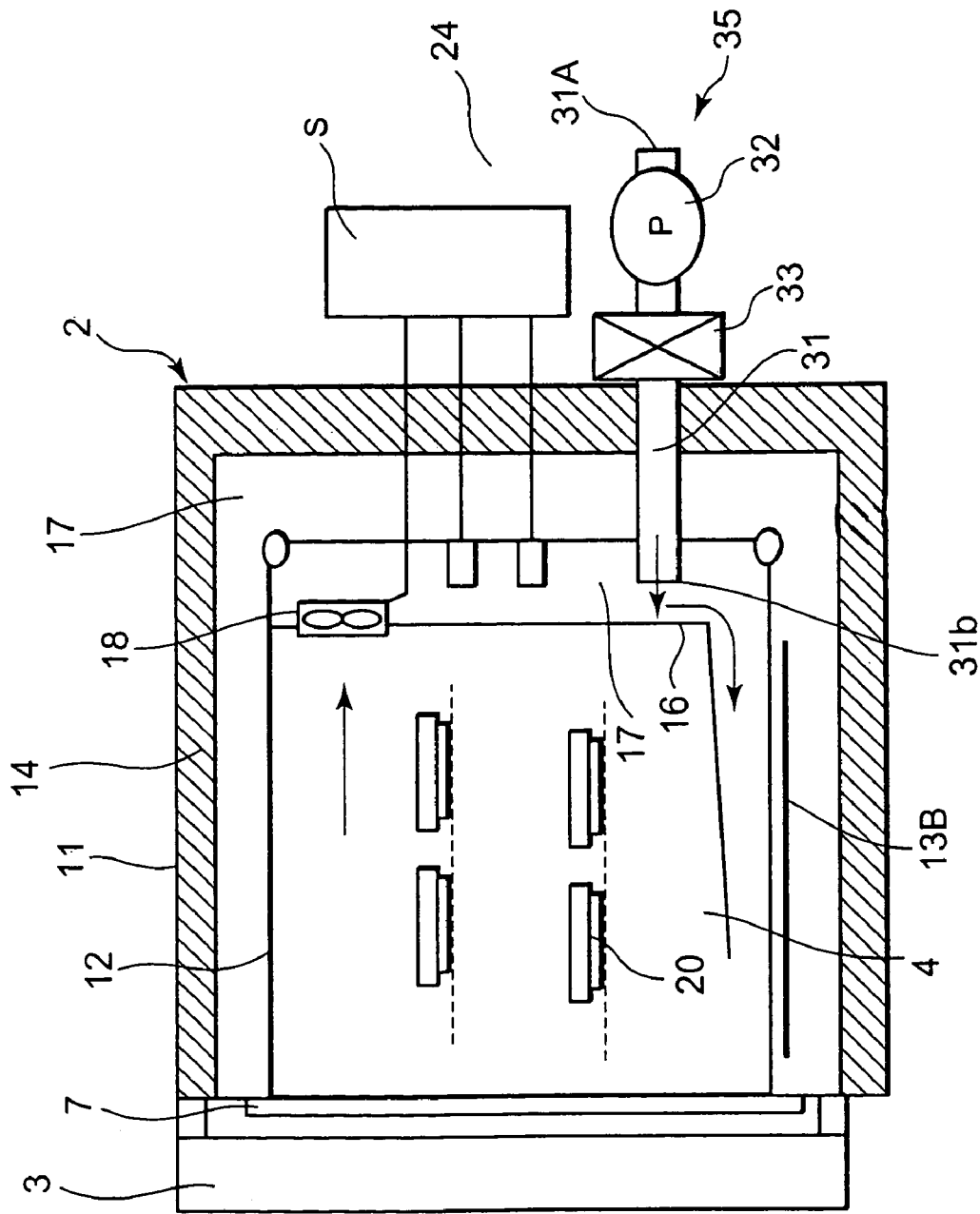
FIG. 4 is a sectional view of an incubator seen from the right according to a second embodiment of the invention.

Next, a second embodiment of the present invention will be described with reference to FIG. 4. Reference numerals similar to those of the first embodiment denote similar functions. As shown in FIG. 4, pressure adjustment means 35 of the second embodiment of the invention comprises a suction tube 31 with a suction pump 32 one end opening 31A of which is positioned in an outside space 34 of an incubator 1 and the other end opening 31B of which is positioned in an air passage 17 in a storeroom 4 of the incubator 1, and a suction filter 33 for bacteria elimination which is disposed on a downstream side of the suction pump 32 of the suction tube 31.

In FIG. 4, by arranging the suction pump 32 and the suction filter 33 of the pressure adjustment means 35 outside the incubator 1, mounting or maintenance work of the pressure adjustment means 35 can be carried out independently from the outside. Since an end of an exit side of the suction tube 31 faces the air passage 17, the suction filter 33 can be arranged in the air passage 17 if there is an extra space therein. Additionally, the end of the exit side of the suction tube 31 may be directly extended to the storeroom 4.

According to the pressure adjustment means 35 of the second embodiment, pressure of the incubation room 4 can be set higher than air pressure outside the incubator 1 by the suction tube 31. Thus, air can be guided from the incubation room 4 to an air layer 15 or the outside space 34, and the incubator is very advantageous for safety and hygiene. Air guided into the incubation room 4 by the suction pump 32 can be subjected to bacteria elimination by the suction filter 33. Even if air in which bacterias have been bred is introduced from the outside, the air can be guided to the incubation room 4 in a bacteria eliminated state by the filter 33, thereby improving the safety of the incubator 1. Moreover, since the air guided by the suction pump 32 can be directly guided not to the incubation room 4 but to the air passage 17, the suction filter 33 can be arranged in the air passage 17 if there is an extra space therein. The air passage 17 itself can be effectively used as a cushion (flowing-in space) of the outside air, and air convection can be realized in the air passage 17 by flowing-in air directed by the suction tube 31. As a result, it is possible to stop a circulation fan 18 during an operation of the suction pump 32.

Embodiment 3

Figure 5:
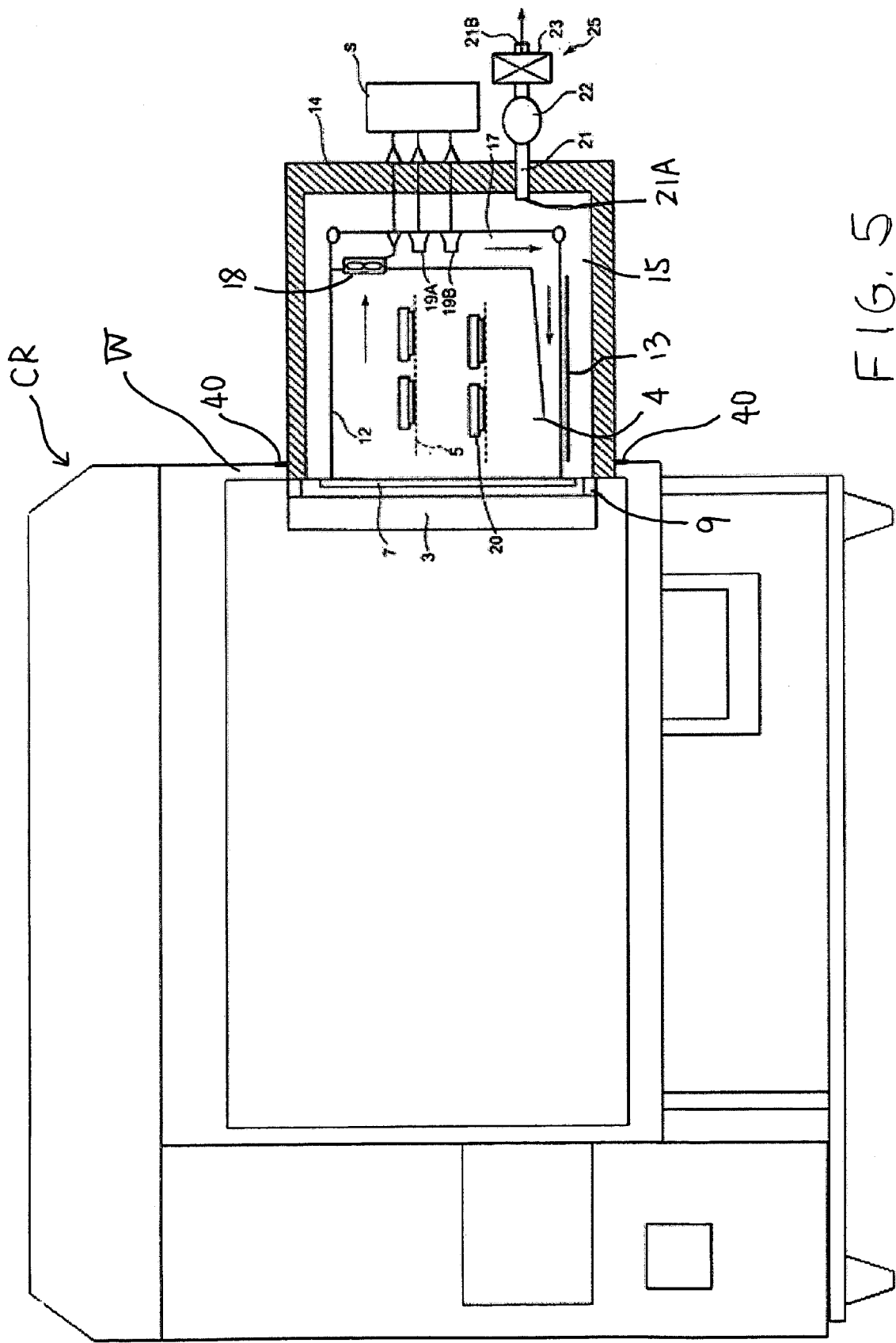
FIG. 5 is a sectional view of an incubator seen from the right according to each of third to fifth embodiments of the present invention.

Next, a third embodiment of the present invention will be described with reference to FIG. 5. Reference numerals similar to those of the first embodiment denote similar functions. As shown in FIG. 5, an incubator 1 of the third embodiment of the invention comprises an adiabatic box main body 2 having an opening on its front, a transparent inner door 7 mounted to the adiabatic box main body 2 to be opened/closed and to close the opening to be opened/closed, and a storeroom 4 surrounded with the inner door 7 and the adiabatic box main body 2 to incubate samples such as cells or microbes. The adiabatic box main body 2 comprises a metal outer box 11, a metal, e.g., stainless steel, antibacterial inner box 12, a heat insulating material 14 arranged in the outer box between the outer box 11 and the inner box 12, and an air layer is arranged more inside than the heat insulating material 14. A partition wall 40 is disposed on the adiabatic box main body 2 to divide outside space 42 of the incubator into front and rear portions. To reduce pressure of the space 42 after the partition wall 40 of the incubator 1 more than that of the storeroom 4, an exhaust tube 21 with an exhaust fan 22 is disposed at one end opening 21A of which is positioned in the air layer 15 and the other end opening 21b of which is positioned in the outside space 42 of the incubator 1. An exhaust filter 23 for bacteria elimination is disposed on a downstream side of the exhaust fan 22 of the exhaust tube 21.

On the other hand, in FIG. 5, an example of aligning a position of the partition wall with a font end of the adiabatic box main body 2 is indicated by a dashed line 40B. According to the partition wall 40B, the outside space of the incubator 1 can be divided into a front space 41 and a rear space 44. In this case, when the incubator 1 is arranged through one wall of a clean room, a space projected in the clean room can be limited to a minimum, and mounting or maintenance work of the incubator 1 can be independently carried out from the outside. Thus, versatility of the incubator can be expanded.

Additionally, an example of aligning the position of the partition wall with a rear end of the adiabatic box main body 2 is indicated by a chain double-dashed line 40C. According to the partition wall 40C, the outside space of the incubator 1 can be divided into a front space 41 and a rear space 43. In this case, when the incubator 1 is arranged through one wall of the clean room, a space projected outside the clean room can be limited to a minimum.

According to the third embodiment, by disposing the partition wall 40 which divides the outside space of the incubator into front and rear portions, air convection of the outside space of the incubator 1 (especially, directed from the partition wall rear side to the front side) can be prevented by the partition wall 40. Even if bacterias enter the outside air, it is possible to surely block/prevent the flowing-in of the air to the front side of the incubator 1 by the partition wall 40. Moreover, by setting pressure of the space 42 after the partition wall 40 of the incubator 1 lower than that of the storeroom 4, an air flow from the storeroom 4 to the rear space 42 of the partition wall 40 can be formed, and flowing-in of the outside air from the rear space 42 of the partition wall 40 to the storeroom 4 can be conversely blocked, whereby safety of the incubator 1 can be further enhanced.

As discussed above in detail, according to the present invention, since the pressure of the storeroom (incubation room) (4) is higher than that of the outside space (24) of he incubator (1), the entry of air from the air layer (15) to the incubation room (4) is blocked even when the air is discharged from the incubation room to the air layer (15) formed around the same. As a result, no air flow is generated from the outside space of the incubator (1) to the incubation room (4), and it is possible to prevent the entry of contaminated outside air.

According to the invention, since the air of the air layer (15) is discharged through the exhaust tube (21), the pressure of the air layer (15) can be set lower compared with that of the incubation room (4). The entry of the air of the air layer (15) into the incubation room (4) can be blocked even if there is a small hole in the inner box (12) and the air leaks from the incubation room (4) to the air layer (15).

According to the invention, since the air of the air layer (15) discharged by the exhaust filter (23) through the exhaust tube (21) to the outside can be subjected to bacteria elimination, even if the air leaks from the incubation room (4) in which bacterias have been bred to the air layer (15), the air can be discharged from the incubation room (4) to the outside in the bacteria-eliminated state, and thus the incubator is advantageous for safety and hygiene.

According to the invention, the pressure of the storeroom (incubation room) 4 can be set higher than the air pressure outside the incubator by the suction tube (31). Thus, the air can be guided from the incubation room (4) to the air layer (15) or the outside space (34), and the incubator (1) is very advantageous for safety and hygiene.

According to the invention, the air guided into the incubation room (4) by the suction pump (32) can be subjected to bacteria elimination by the suction filter (33). Even if the air in which bacterias have been bred is introduced from the outside (34), the air can be guided to the incubation room (4) in the bacteria eliminated state by the filter (33), thereby improving the safety of the incubator (1).

According to the invention, the heat of the heaters (13A), (13B) disposed in the inner box (12) is guided in a wide range in the incubation room (4) through heat transfer of the metal inner box (12), and the natural air convection which uses the air of the air layer (15) is generated. Accordingly, heating can be carried out through air transfer even in a direction to the surface of no heater. Besides, in addition to the temperature in the incubation room (4), the humidity can be adjusted by using the heat of the heater (13A) to heat the humidifying tray (6).

According to the invention, by constituting the heater (13A) arranged in the bottom surface of the inner box and the heaters (13B) arranged in both left and right side faces of the inner box of different circuits, it is possible to control the heating of the humidifying tray (6) independently of the heating in the incubation room (4), thereby facilitating adjustment of the temperature and the humidity of the incubator (1).

According to the invention, since the air guided by the suction pump (32) can be directly guided not to the incubation room (4) but to the air passage (17), the suction filter (33) can be arranged in the air passage (17) if there is an extra space therein. The air passage (17) itself can be effectively used as a cushion (flowing-in space) of the outside air, and air convection can be realized in the air passage (17) by flowing-in air directed by the suction tube (31). As a result, it is possible to stop the circulation fan (18) during the operation of the suction pump (32).

According to the invention, by disposing the partition wall (40) which divides the outside space of the incubator into front and rear portions, air convection of the outside space of the incubator (1) (especially, directed from the partition wall rear side to the front side) can be prevented by the partition wall (40). Even if bacterias enter the outside air, it is possible to surely block/prevent the flowing-in of the air to the front side of the incubator (1) by the partition wall (40).

According to the invention, by setting the pressure of the space (42) after the partition wall (40) of the incubator (1) lower than that of the storeroom (4), an air flow from the storeroom (4) to the rear space (42) of the partition wall (40) can be formed, and flowing-in of the outside air from the rear space (42) of the partition wall (40) to the storeroom (4) can be conversely blocked, whereby safety of the incubator (1) can be further enhanced.

Furthermore, according to the invention, by the sealing member (2B) which seals the transparent inner door (7) to the main body (2), it is possible to block air leakage from the opening of the adiabatic box main body (2) to the outside of the inner door (7), and flowing of outside air from the outside of the inner door (7) through the opening into the incubation room (4).

What is claimed is:

1. A combination of an incubator and a clean room, the incubator comprising:
   an adiabatic box main body having an opening on a front face thereof,
   a transparent inner door mounted to the adiabatic box main body to be opened/closed and to close the opening to be opened, and
   a storeroom surrounded with the inner door and the adiabatic box main body to incubate samples such as cells or microbes,
   wherein the adiabatic box main body comprises a metal outer box, a metal inner box, a heat insulating material arranged in the outer box between the outer box and the inner box, and an air layer arranged more inside than the heat insulating material, and a partition wall is disposed on, and extends outwardly from, the adiabatic box main body, such that when the incubator, with the partition wall, is arranged to extend through one wall of the clean room, the incubator and the partition wall divides an inside of the clean room from an outside thereof by combination of the incubator with the clean room, and wherein air pressure in the storeroom is higher than air pressure outside the incubator.

2. The combination according to claim 1, wherein a sealing member is disposed in the opening of the adiabatic box main body to seal the inner door to the main body.

* * * * *